US008900573B2

(12) United States Patent
Davies et al.

(10) Patent No.: US 8,900,573 B2
(45) Date of Patent: Dec. 2, 2014

(54) IMMUNE PRIVILEGED AND MODULATORY PROGENITOR CELLS

(71) Applicants: John E. Davies, Toronto (CA); Jane Ennis, Toronto (CA); Alejandro Gomez-Aristiz-Abal, Toronto (CA); Dolores Baksh, Mississauga (CA)

(72) Inventors: John E. Davies, Toronto (CA); Jane Ennis, Toronto (CA); Alejandro Gomez-Aristiz-Abal, Toronto (CA); Dolores Baksh, Mississauga (CA)

( * ) Notice: Subject to any disclaimer, the term of this patent is extended or adjusted under 35 U.S.C. 154(b) by 0 days.

(21) Appl. No.: 13/630,312

(22) Filed: Sep. 28, 2012

(65) Prior Publication Data

US 2013/0089565 A1 Apr. 11, 2013

Related U.S. Application Data

(63) Continuation of application No. 12/299,736, filed as application No. PCT/CA2007/000781 on May 4, 2007, now Pat. No. 8,277,794.

(60) Provisional application No. 60/746,500, filed on May 5, 2006.

(51) Int. Cl.
| | |
|---|---|
| *A01N 65/00* | (2009.01) |
| *A01N 63/00* | (2006.01) |
| *C12N 5/00* | (2006.01) |
| *C12N 5/02* | (2006.01) |
| *C12N 5/071* | (2010.01) |
| *C12N 5/0775* | (2010.01) |
| *A61K 35/44* | (2006.01) |
| *A61K 35/12* | (2006.01) |

(52) U.S. Cl.
CPC ............. *A61K 35/12* (2013.01); *C12N 5/0665* (2013.01); *A61K 35/44* (2013.01)
USPC ...... 424/93.7; 424/93.1; 424/184.1; 435/325; 435/372

(58) Field of Classification Search
None
See application file for complete search history.

(56) References Cited

U.S. PATENT DOCUMENTS

| | | | |
|---|---|---|---|
| 5,919,702 A | 7/1999 | Purchio et al. | |
| 7,122,178 B1 | 10/2006 | Simmons et al. | |
| 7,547,546 B2 | 6/2009 | Davies et al. | |
| 2003/0161818 A1 | 8/2003 | Weiss et al. | |
| 2004/0136967 A1 | 7/2004 | Weiss et al. | |
| 2004/0137612 A1 | 7/2004 | Baksh et al. | |
| 2005/0019911 A1 | 1/2005 | Gronthos et al. | |
| 2005/0148074 A1 | 7/2005 | Davies et al. | |
| 2005/0158289 A1 | 7/2005 | Simmons et al. | |
| 2005/0281790 A1 | 12/2005 | Simmons et al. | |
| 2006/0008452 A1 | 1/2006 | Simmons et al. | |
| 2006/0193840 A1 | 8/2006 | Gronthos et al. | |
| 2006/0199263 A1 | 9/2006 | Auger et al. | |
| 2006/0286077 A1 | 12/2006 | Gronthos et al. | |
| 2008/0020459 A1 | 1/2008 | Baksh et al. | |
| 2008/0113434 A1 | 5/2008 | Davies et al. | |
| 2009/0047277 A1 | 2/2009 | Reed et al. | |

FOREIGN PATENT DOCUMENTS

| | | |
|---|---|---|
| WO | WO-91/09521 A1 | 7/1991 |
| WO | WO 01/11011 | 2/2001 |
| WO | WO 02/086104 | 10/2002 |
| WO | WO 2004/072273 | 8/2004 |
| WO | WO 2005/001076 | 1/2005 |
| WO | WO 2005/027633 | 3/2005 |
| WO | WO 2005/038012 | 4/2005 |
| WO | WO 2005/085428 | 9/2005 |
| WO | WO 2006/019357 | 2/2006 |
| WO | WO 2007/071048 | 6/2007 |
| WO | WO 2007/099534 | 9/2007 |
| WO | WO 2007/128115 | 11/2007 |

OTHER PUBLICATIONS

Aggarwal et al., "Human Mesenchymal Stem Cells Modulate Allogeneic Immune Cell Responses," *Blood* 105:1815-1822 (2005).
Aubin, "Bone Stem Cells," *J. Cell. Biochem. Suppl.* 72(S30-31):73-82 (1998).
Beckstead et al., "Enzyme Histochemistry and Immunohistochemistry on Biopsy Specimens of Pathologic Human Bone Marrow," *Blood* 57(6):1088-1098 (1981).
Beckstead et al., "Enzyme Histochemistry on Bone Marrow Biopsies: Reactions Useful in the Differential Diagnosis of Leukemia and Lymphoma Applied to 2-Micron Plastic Sections," *Blood* 55(3):386-394 (1980).
Bianco et al., "Uno, Nessuno e Centomila: Searching for the Identity of Mesodermal Progenitors," *Experimental Cell Research* 251:257-263 (1999).
Bieback et al., "Critical Parameters for the Isolation of Mesenchymal Stem Cells from Umbilical Cord Blood," *Stem Cells* 22:625-634 (2004).
Can et al., "Concise Review: Human Umbilical Cord Stroma with Regard to the Source of Fetus-Derived Stem Cells," *Stem Cells* 25:2886-2895 (2007).
Canfield et al., "Osteogenic Potential of Vascular Pericytes," *Bone Engineering* [JE Davies ed.] EM Squared, Inc., Toronto, Canada. 143-151 (2000).
Caplan, "Mesenchymal Stem Cells," *J. Orthop. Res.* 9:641-650 (1991).
Chacko and Reynolds, "Architecture of Distended and Nondistended Human Umbilical Cord Tissues, with Special Reference to the Arteries and Veins," *Carnegie Institute of Washington, Contributions to Embryology* 237:135-150 (1954).
Conget et al., "Phenotypical and Functional Properties of Human Bone Marrow Mesenchymal Progenitor Cells," *J. Cell Physiol.* 181:67-73 (1999).
Corcione et al., "Human Mesenchymal Stem Cells Modulate B-Cell Functions," *Blood* 107:367-372 (2006).
Di Nicola et al., "Human Bone Marrow Stromal Cells Suppress T-Lymphocyte Proliferation Induced by Cellular or Nonspecific Mitogenic Stimuli," *Blood* 99:3838-3843 (2002).
Djouad et al., "Immunosuppressive Effect of Mesenchymal Stem Cells Favors Tumor Growth in Allogenic Animals," *Blood* 102:3837-3844 (2003).

(Continued)

*Primary Examiner* — Valarie Bertoglio
(74) *Attorney, Agent, or Firm* — Clark & Elbing LLP; Paul T. Clark, Esq.; Todd Armstrong

(57) ABSTRACT

Described herein is a method for modulating an immune reaction between lymphocytes and a body recognized by the lymphocytes as foreign. The method exploits the immunomodulating activity of a new class of progenitor cells termed HUCPVCs derived from the perivascular region of human umbilical cord. The method can also emply soluble factors exuded by cultured HUCPVCs. The method is useful to treat immune disorders including graft versus host disease, autoimmune disorders, and the like.

16 Claims, 8 Drawing Sheets

(56) References Cited

OTHER PUBLICATIONS

Figure 1:
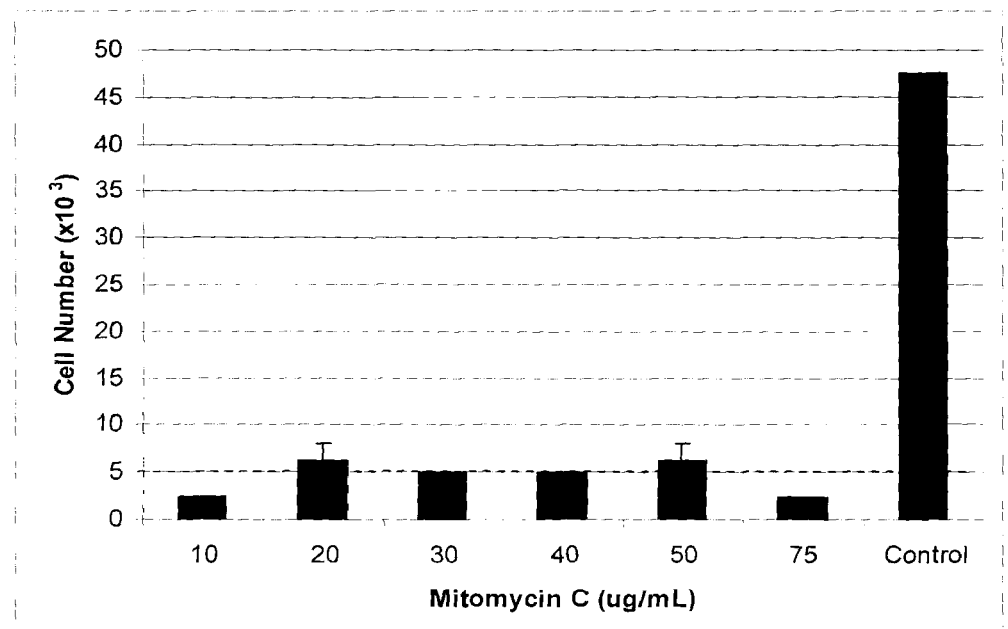

Ennis et al., "In vitro immunologic properties of human umbilical cord perivascular cells," *Cytotherapy* 10: 174-171 (2008).
Etherington, "Proteinases in Connective Tissue Breakdown." *Ciba Found. Symp.* 75:87-103 (1979). [Abstract Only].
Friedenstein et al., "Fibroblast Precursors in Normal and Irradiated Mouse Hematopoietic Organs," *Exp. Hematol.* 4:267-274 (1976).
Friedman et al., "Umbilical Cord Mesenchymal Stem Cells: Adjuvants for Human Cell Transplantation," *Biol. Blood Marrow Transplant* 13:1477-1486 (2007).
Götherström et al., Immunomodulatory effects of human foetal liver-derived mesenchymal stem cells, *Bone Marrow Transplant* 32: 265-272 (2003).
Gronthos et al., "Postnatal Human Dental Pulp Stem Cells (DPSCs) in vitro and in vivo." *Proc. Natl. Acad. Sci. USA* 97(25):13625-13630 (2000).
Hamada et al., "Mesenchymal stem cells (MSC) as therapeutic cytoreagents for gene therapy," *Cancer Sci.* 96:149-156 (2005).
Haynesworth et al., "Cell-Based Tissue Engineering Therapies: The Influence of Whole Body Physiology," *Adv. Drug Deliv. Rev.* 33:3-14 (1998).
Horwitz et al., "Transplantability and Therapeutic Effects of Bone Marrow-Derived Mesenchymal Cells in Children with Osteogenesis Imperfecta," *Nature Medicine* 5:309-313 (1999).
Hu et al., "Abundant Progenitor Cells in the Adventitia Contribute to Atherosclerosis of Vein Grafts in ApoE-deficient Mice," *J. Clin. Invest.* 113(9):1258-1265 (2004).
Karahuseyinoglu et al., "Functional Structure of Adipocytes Differentiated from Human Umbilical Cord Stroma-Derived Stem Cells," *Stem Cells* 26:682-691 (2008).
Kogler et al., "A New Human Somatic Stem Cell From Placental Cord Blood with Intrinsic Pluripotent Differentiation Potential," *J. Exp. Med.* 200(2):123-135 (2004).
Kulkarni et al., "Absence of Wharton's Jelly Around the Umbilical Arteries," *Indian J. Pediatr.* 74(8):787-789 (2007).
Le Blanc, "Immunomodulatory effects of fetal and adult mesenchymal stem cells," *Cytotherapy* 5: 485-489 (2003).
Le Blanc et al., "Immunobiology of human mesenchymal stem cells and future use in hematopoietic stem cell transplantation," *Biol Blood Marrow Transplant.* 33: 321-334 (2005).
Le Blanc et al., "Treatment of severe acute graft-versus-host disease with third party haploidentical mesenchymal stem cells," *Lancet* 363: 1439-1441 (2004).
Li et al., "Mesenchymal Stem Cells Derived from Human Placenta Suppress Allogeneic Umbilical Cord Blood Lymphocyte Proliferation," *Cell Research* 15:539-547 (2005).
Lu et al., "Stem Cells from Bone Marrow, Umbilical Cord Blood and Peripheral Blood for Clinical Application: Current Status and Future Application," *Crit. Rev. Oncol. Hematol.* 22: 61-78 (1996) (Abstract Only).
Ma et al., "Human Umbilical Cord Wharton's Jelly-Derived Mesenchymal Stem Cells Differentiation into Nerve-Like Cells," *Chinese Medical Journal* 118:1987-1993 (2005).
Maccario et al., "Interaction of Human Mesenchymal Stem Cells with Cells Involved in Alloantigen-Specific Immune Response Favors the Differentiation of CD4+ T-Cell Subsets Expressing a Regulatory/Suppressive Phenotype," *Haematologica* 90:516-525 (2005).
Maitra et al., "Human Mesenchymal Stem Cells Support Unrelated Donor Hematopietic Stem Cells and Suppress T-Cell Activation," *Bone Marrow Transplantation* 33:597-604 (2004).
Minguell et al., "Mesenchymal Stem Cells," *Exp. Biol. Med.* 226(6):507-520 (2001).
Mitchell et al., "Matrix Cells from Wharton's Jelly Forms Neurons and Glia," *Stem Cells* 21:50-60 (2003).
Nanaev et al., "Stromal Differentiation and Architecture of the Human Umbilical Cord," *Placenta* 18:53-64 (1997).
Naughton et al., "Cells Isolated from Wharton's Jelly of the Human Umbilical Cord Develop a Cartilage Phenotype When Treated with TGFβ in vitro," *Faseb Journal* 11:A19 (1997). [Abstract only].
Parry, "Some Electron Microscope Observations on the Mesenchymal Structures of Full-Term Umbilical Cord," *Journal of Anatomy* 107:505-518 (1970).
Pennati, "Biomechanical Properties of the Human Umbilical Cord," *Biorheology* 38:355-366 (2001).
Pereda et al., "New Advances in Human Embryology: Morphofunctional Relationship Between the Embryo and the Yolk Sac," *Medical Electron Micropscopy* 35:67-78 (1999).
Romanov et al., "Searching for Alternative Sources of Postnatal Human Mesenchymal Stem Cells: Candidate MSC-Like Cells from Umbilical Cord," *Stem Cells* 21:105-110 (2003).
Sarugaser et al., "Human Umbilical Cord Wharton's Jelly as a Source of Mesenchymal Progenitors Capable of Expressing a Functional Osteogenic Phenotype," Podium Presentation—Tissue Engineering Society International Orlando, FL (2003).
Sarugaser et al., "Human Umbilical Cord Perivascular Cells as a Source of Mesenchymal Progenitors Capable of Expressing a Functional Osteogenic Phenotype," Poster Presentation—World Biomaterials Congress, Sydney, NSW, Australia (2004).
Sarugaser et al., "Human Umbilical Cord Perivascular (HUCPV) Cells: A Source of Cells for Allogeneic Cells Based Therapies," Podium Presentation—European Tissue Engineering Society, Lausanne, Switzerland (2004).
Sarugaser et al., "Human Umbilical Cord Perivascular (HUCPV) Cells: A Source of Mesenchymal Progenitors," *Stem Cells* 23:220-229 (2005).
Sarugaser et al., "Human Umbilical Cord Wharton's Jelly as a Source of Mesenchymal Progenitors Capable of Expressing a Functional Osteogenic Phenotype," Podium Presentation—Orthopaedic Research Society, San Francisco, CA (2004).
Sartore et al., "Contribution of Adventitial Fibroblasts to Neointima Formation and Vascular Remodeling: From Innocent Bystander to Active Participant," *Circulation Research* 89:1111-1121 (2001).
Schoenberg et al., "Studies on Connecting Tissue v. Fiber Formation in Wharton's Jelly," *Laboratory Investigation* 9(3):350-355 (1960).
Sen et al., "Adipogenic Potential of Human Adipose Derived Stromal Cells from Multiple Donors is Heterogeneous," *J. Cell. Biochem.* 81:312-319 (2001).
Shi et al., "Perivascular Niche of Postnatal Mesenchymal Stem Cells in Human Bone Marrow and Dental Pulp," *J. Bone and Mineral Res.* 18:696-704 (2003).
Sotiropoulou et al., "Interactions Between Human Mesenchymal Stem Cells and Natural Killer Cells," *Stem Cells* 24:74-85 (2006).
Spaggiari et al., "Mesenchymal Stem Cell-Natural Killer Cell Interactions: Evidence that Activated NK Cells are Capable of Killing MSCs. Whereas MSCs Can Inhibit IL-2-Induced NK-Cell Proliferation," *Blood* 107:1484-1490 (2006).
Stenmark et al., "Hypoxic Activation of Adventitial Fibroblasts: Role in Vascular Remodeling," *Chest* 122(6):326-334 (2002).
Takechi et al., "Ultrastructural and Immunohistochemical Studies of Wharton's Jelly Umbilical Cord Cells," *Placenta* 14:235-245 (1993).
Tuchmann-Duplessis et al., "Illustrated Human Embryology," Springer-Verlag, New York, NY 14-61 (1972).
Wang et al., "Mesenchymal Stem Cells in the Wharton's Jelly of Human Umbilical Cord," *Stem Cells* 22:1330-1337 (2004).
Wharton, "Adenographia," Oxford, UK, Oxford Univ. Press, 242-248 (1996).
Weiss, "Histology: Cell and Tissue Biology," *Elsevier Biomedical* New York, NY, 997-998 (1983).
Weiss et al., "Human Umbilical Cord Matrix Stem Cells: Preliminary Characterization and Effect of Transplantation in a Rodent Model of Parkinson's Disease," *Stem Cells* 24:781-792 (2006); and Supplemental Tables and Figures from web Edition (16 pp.).
Examination Report for Australian Application No. 2007247725, issued Dec. 9, 2011 (2 pages).
Examination Report No. 2 for Australian Application No. 2007247725, issued Nov. 7, 2012 (2 pages).
Extended European Search Report for Application No. 07719706.9, issued Feb. 24, 2012 (4 pages).
International Preliminary Report on Patentability for Application No. PCT/CA2007/00781, issued on Nov. 11, 2008 (8 pages).
International Search Report for Application No. PCT/CA2007/00781, completed Jun. 27, 2007 (5 pages).
International Preliminary Report on Patentability for Application No. PCT/CA2006/002092, issued on Jun. 24, 2008 (7 pages).

Figure 13

A. BMSC derived MSCs

| RPS27A | (AKT1) | (ANGPT1) | (ANGPT2) | (APAF1) | (ATM) | (BAD) | (BAI1) |
|---|---|---|---|---|---|---|---|
| (BAX) | (BCL2) | (BCL2L1) | (BIRC5) | (BRCA1) | (BRCA2) | (CASP8) | (CASP9) |
| (CCND1) | (CCNE1) | (CD44) | (CDC25A) | (CDH1) | (CDK2) | (CDK4) | CDKN1A |
| (CDKN1B) | (CDKN2A) | (CFLAR) | (CHEK2) | (COL18A1) | (CTNNB1) | (E2F1) | (EGF) |
| (EGFR) | (ERBB2) | (ETS2) | (FGF2) | (FGFR2) | (FLT1) | FOS | (G2MA) |
| (HGF) | (HTATIP2) | (ICAM1) | (IFNA1) | (IFNB1) | IGF1 | IL8 | (ITGA1) |
| (ITGA2) | ITGA3 | (ITGA4) | (ITGA5) | (ITGA6) | (ITGAV) | ITGB1 | (ITGB3) |
| ITGB5 | JUN | (KAI1) | (KISS1) | (MAP2K1) | (MAPK14) | (MCAM) | (MDM2) |
| (MET) | (MICA) | MMP1 | MMP2 | (MMP9) | (MTA1) | (MTA2) | (MTSS1) |
| MYC | (NCAM1) | NFKB1 | NFKBIA | NME1 | (NME4) | (PDGFA) | (PDGFB) |
| (PIK3CB) | (PIK3R1) | PLAU | PLAUR | (PNN) | (PRKDC) | (PTEN) | (RAF1) |
| (RASA1) | RB1 | S100A4 | (SERPINB2) | (SERPINB5) | (SERPINE1) | SNCG | (SRC) |
| (SYK) | (TEK) | (TERT) | (TGFB1) | (TGFBR1) | THBS1 | THBS2 | TIMP1 |
| TIMP3 | (TNF) | TNFRSF10B | TNFRSF1A | (TNFRSF25) | (FAS) | (TP53) | (TWIST1) |
| (UCC1) | (VEGF) | (PUC18) | (Blank) | Blank | AS1R2 | AS1R1 | AS1 |
| GAPDH | B2M | HSPCB | HSPCB | ACTB | ACTB | BAS2C | BAS2C |

B. HUCPVCs

| RPS27A | AKT1 | (ANGPT1) | (ANGPT2) | (APAF1) | (ATM) | (BAD) | (BAI1) |
|---|---|---|---|---|---|---|---|
| (BAX) | (BCL2) | (BCL2L1) | (BIRC5) | (BRCA1) | (ERCA2) | (CASP8) | (CASP9) |
| (CCND1) | (CCNE1) | (CD44) | (CDC25A) | (CDH1) | (CDK2) | CDK4 | CCKN1A |
| (CDKN1B) | (CDKN2A) | (CFLAR) | (CHEK2) | (COL18A1) | (CTNNB1) | (E2F1) | (EGF) |
| (EGFR) | (ERBB2) | (ETS2) | (FGF2) | (FGFR2) | (FLT1) | (FOS) | (G2MA) |
| (HGF) | (HTATIP2) | (ICAM1) | (IFNA1) | (IFNB1) | IGF1 | IL8 | ITGA1 |
| (ITGA2) | ITGA3 | (ITGA4) | (ITGA5) | (ITGA6) | (ITGAV) | ITGB1 | (ITGB3) |
| ITGB5 | (JUN) | (KA1) | (KISS1) | (MAP2K1) | (MAPK14) | (MCAM) | (MDM2) |
| (MET) | (MICA) | MMP1 | MMP2 | (MMP9) | (MTA1) | (MTA2) | (MTSS1) |
| MYC | (NCAM1) | NFKB1 | NFKBIA | NME1 | (NME4) | (PDGFA) | (PDGFB) |
| (PIK3CB) | (PIK3R1) | PLAU | PLAUR | PNN | (PRKDC) | PTEN | (RAF1) |
| (RASA1) | RB1 | S100A4 | (SERPINB2) | (SERPINB5) | SERPINE1 | SNCG | (SRC) |
| (SYK) | (TEK) | (TERT) | (TGFB1) | (TGFBR1) | THBS1 | THBS2 | TIMP1 |
| TIMP3 | (TNF) | TNFRSF10B | TNFRSF1A | (TNFRSF25) | (FAS) | (TP53) | (TWIST1) |
| (UCC1) | (VEGF) | (PUC1B) | (Blank) | Blank | AS1R2 | AS1R1 | (AS1) |
| GAPDH | B2M | HSPCB | HSPCB | ACTB | ACTB | BAS2C | BAS2C |

IMMUNE PRIVILEGED AND MODULATORY PROGENITOR CELLS

CROSS-REFERENCE TO RELATED APPLICATIONS

This application is a continuation of U.S. patent application Ser. No. 12/299,736 (now U.S. Pat. No. 8,277,794), having a 371 (c) date of Jul. 8, 2009, which is the U.S. National Stage filing under 35 U.S.C. §371 of International Application No. PCT/CA2007/000781, filed May 4, 2007, which claims benefit of U.S. Provisional Patent Application No. 60/746,500, filed May 5, 2006.

FIELD OF THE INVENTION

This invention relates to progenitor cells that are immuno-privileged and/or immunomodulatory, their production, their formulation, and their therapeutic use.

BACKGROUND TO THE INVENTION

Adult bone marrow (BM) is the most common source of mesenchymal stem/progenitor cells (MSCs), (also called Mesenchymal Stromal Cells[1]) which are functionally defined by their capability of differentiating into the skeletal tissues: bone[2-4], cartilage[5-7], fat[8] and muscle[9] in vitro. MSCs are classically distinguished from the heterogeneous milieu of cells through adhesion to tissue culture plastic and the formation of colony unit-fibroblasts (CFU-Fs), the frequency of which are 1:100,000-1:500,000 nucleated cells in adult marrow[10], and studies have now identified a suite of markers with which MSCs are categorized[10,11]. This low proportion of MSCs leads to the necessity of culture expansion and selection before use to attain the appropriate cell numbers for any kind of cellular therapy. There are other emerging sources of MSCs such as: adipose tissue[12], trabecular bone[13] and fetal liver[14] which have a CFU-F frequency of: 1:32[15], 1:636[13] and 1:88,495[14] respectively. While adipose tissue does appear to have the highest frequency of progenitors, the doubling time of those cells ranges between 3.6 to 4.4 days[15], and the extraction procedure is complicated, invasive, and lengthy[12]. Harvesting trabecular bone results in low cell yield (89×10$^6$ cells/gram of bone from young donors[13]), especially when combined with the CFU-F frequency; and is extremely invasive resulting in donor site morbidity.

Unique among these new sources of MSCs are human umbilical cord perivascular cells (HUCPVCs), which are an easily accessible, highly proliferative source of cells with a population doubling time of 20 hours (dependent on serum)[16]. The frequency of CFU-Fs in HUCPVCs is 1:300 at passage 0 but increases to 1:3 at passage 1[17], which is orders of magnitude higher than bone marrow[16]. Therefore HUCPVCs represent a population of cells with an extremely high proportion of MSCs which proceed to divide very quickly, thus making them an excellent candidate for clinical mesenchymal therapies. These cells have been used in various assays to determine their marker expression phenotype and differentiation potential[16,18], and have been found to be either bioequivalent to, or perform better than, BM-MSCs.

In addition to their ability to differentiate, MSCs also have potential immunological uses as BM-MSCs have been shown to be both immunoprivileged and immunomodulatory[19-21]. These terms refer to a cell's ability to evade recognition from a mismatched host's immune system, and the ability to mitigate an ongoing response by that system, respectively. MSCs from several sources other than bone marrow have been tested for their immunogenicity in in vitro cultures. MSCs from adipose tissue derived from adult dermolipectomies were shown to be capable of both immunoprivilege and immunomodulation in vitro[22], whereas fetal liver cells were found to be capable of avoiding a mismatched immune response, however they were not able to modulate alloreactivity caused by two mismatched populations of lymphocytes[23,24]. Thus, the source of MSCs directly affects those cells' immunogenic capabilities.

This in vitro work has begun to be validated in the clinical setting; for example, a boy was rescued from severe acute graft vs. host disease (GvHD) by transfusion of haploidentical bone marrow MSCs from his mother[25]. One year post treatment, in comparison to a cohort of patients suffering from the same level of severity of the disease, he was the only one alive. Since this initial patient, a suite of 8 patients have been treated with BM-MSCs, of which 6 showed a complete remission of symptoms[26]. Allogeneic BM-MSCs have also been used in Crohn's Disease to treat patients who are refractory to current treatments, and this treatment is currently in clinical trials in the United States[27,28]. Fetal liver MSCs have shown efficacy in the early treatment of osteogenesis imperfecta (OI). MSCs from a male fetal liver were transplanted into an unrelated 32 week female fetus with severe OI, who had suffered several intrauterine fractures[29]. Following the transplantation, the remainder of the pregnancy proceeded normally, and there were no further fractures. This patient has been followed up to 2 years after birth, and the child has shown a normal growth curve and has suffered only 3 fractures. Using an XY-specific probe, the patient was found to have 0.3% engraftment in a bone biopsy.

In addition to undifferentiated cells, osteogenically induced rabbit BM-MSCs were found to be immunoprivileged and immunomodulatory in vitro, but when transplanted in vivo the immunomodulatory capacity was lost[30]. This would not affect the function of the cells however; as they only require protection from an immune response in order to fulfill their role. In a more involved induction, murine bone marrow MSCs were manipulated to release erythropoietin and implanted in mice, which resulted in significantly less engraftment compared to un-manipulated controls[31]. Thus, manipulation of MSCs can lead to their loss of immunomodulation and/or immunoprivilege and can be crucial to the survival and function of the graft.

There is evidence to support that the immunoprivilege of MSCs transcends species barriers, and they can be used xenogeneically. This was first demonstrated by Bartholomew et al who used human BM-MSCs in baboons, and showed enhanced skin graft survival[21]. While the end result of this study was positive, the specific fate of the administered cells was not determined. Wang et al. have utilized GFP transfected cells and histological analyses to studied the survival of xenogeneic BM-MSCs, and showed that the cells survive up to the 11 week timepoint without immunosuppression, however there was an increased host immune reaction[32]. MSCs have also been reported to survive in xenogeneic transplantations in two cardiac models[33,34]. In preliminary work with HUCPVCs, the cells were delivered peritoneally in permeable chambers. After 3 weeks, there was no noticeable inflammation noted upon macroscopic visualization[35]. This is encouraging preliminary work indicating the potential for not only the immunoprivilege of HUCPVCs, but also for their ability to test them in animal models without rejection.

The inventors investigated the immunoprivileged and immunomodulatory properties of HUCPVCs in vitro by conducting both: co-cultures of HUCPVCs with unmatched lymphocytes, and mixed lymphocyte cultures (MLCs) populated by two HLA mismatched donors. Also studied were HUCPVC death, lymphocyte proliferation and activation with varying levels of HUCPVCs present in both naïve and activated lymphocyte environments. In addition, the necessity for cell contact for the observation of immunological effects was investigated.

SUMMARY OF THE INVENTION

The inventors now report herein a series of experiments which illustrate both the immunoprivileged and immunomodulatory capabilities of HUCPVCs when tested in one and two-way in vitro mixed lymphocyte cultures (MLCs). Additionally, MLCs were performed which reveal a HUCPVC-induced decrease in activation of previously stimulated lymphocytes. The inventors further show that the HUCPVC immunomodulatory function is mediated through a soluble factor(s) produced upon culturing of the HUCPVCs, as cell contact is not required for the immunomodulatory effect to be observed. Furthermore, the inventors illustrate that HUCPVCs are capable of modulating a two-way in vitro MLC, and describe the use of these cells for cellular therapy applications, particularly to modulate the immune response.

Thus, in one of its aspects, the present invention provides a method for treating a subject having, or at risk of developing, an adverse immune reaction, comprising the step of administering to the subject an immunomodulating effective amount of (1) a cell population comprising, and preferably consisting essentially of, human umbilical cord perivascular cells (HUCPVCs), and/or (2) an immunomodulating soluble factor produced upon culturing of said cells. In related embodiments, the method is applied to treat recipients of allogeneic or xenogeneic grafts, including cells, tissues and organs, to reduce the onset or severity of adverse immune reaction thereto, including graft versus host disease. In a general aspect, the present invention thus provides a method for modulating an immune reaction between lymphocytes, such as peripheral blood lymphocytes, and a body recognized by the lymphocytes as foreign, comprising the step of introducing a formulation comprising a physiologically tolerable vehicle and HUCPV cells or immunomodulating soluble factors that are extractable therefrom, in an amount effective to modulate and particularly to inhibit or reduce that immune reaction.

In a related aspect, the present invention provides for the use of HUCPVC cells or an immunomodulating soluble factor produced thereby in the manufacture of a medicament for the treatment of a subject having or at risk of developing an adverse immune reaction, or for the treatment of a graft prior to transplantation, to mitigate or reduce immune reaction between the graft and recipient.

In another of its aspects, the present invention provides a formulation, in unit dosage form or in multidosage form, comprising an immunomodulating effective amount of HUCPVCs and/or an immunomodulating soluble factor produced thereby, and a physiologically tolerable vehicle therefor.

In a further aspect, the present invention provides an immunomodulating extract, or an immunomodulating fraction thereof, comprising one or more soluble factors produced by cultured HUCPVCs.

In another aspect, the present invention provides a treatment method as described hereinabove, wherein the administered cells are obtained and administered without cryogenic storage.

In a further aspect of the present invention, the administered HUCPVCs are immunoprivileged and immunomodulatory cells. In embodiments, the HUCPVCs are substantially lacking both the MHC class I and MHC class II phenotypes. In a related embodiment, the administered HUCPVCs are obtained by thawing of a population of frozen HUCPVCs.

In a further embodiment of the present invention, the administered immunoprivileged HUCPVCs are engineered genetically, and incorporate a transgene that encodes a heterologous protein of interest, particularly but not exclusively including a protein effective to manage the immune system such as a protein that enhances immunomodulation, and especially a protein that inhibits adverse immune reaction, such as CTLA4.

These and other aspects of the present invention are described in greater detail below, with reference to the accompanying Figures, in which:

BRIEF REFERENCE TO THE FIGURES

FIG. 1: Cell counts of HUCPVCs after 7 days in culture post-MMC treatment (n=2). The cells were treated with ranging concentrations of MMC for 20 minutes at 37° C. at 5% $CO_2$ and assayed for their proliferation. All are seen to be significantly lower than control ($p<0.001$).

Figure 2:
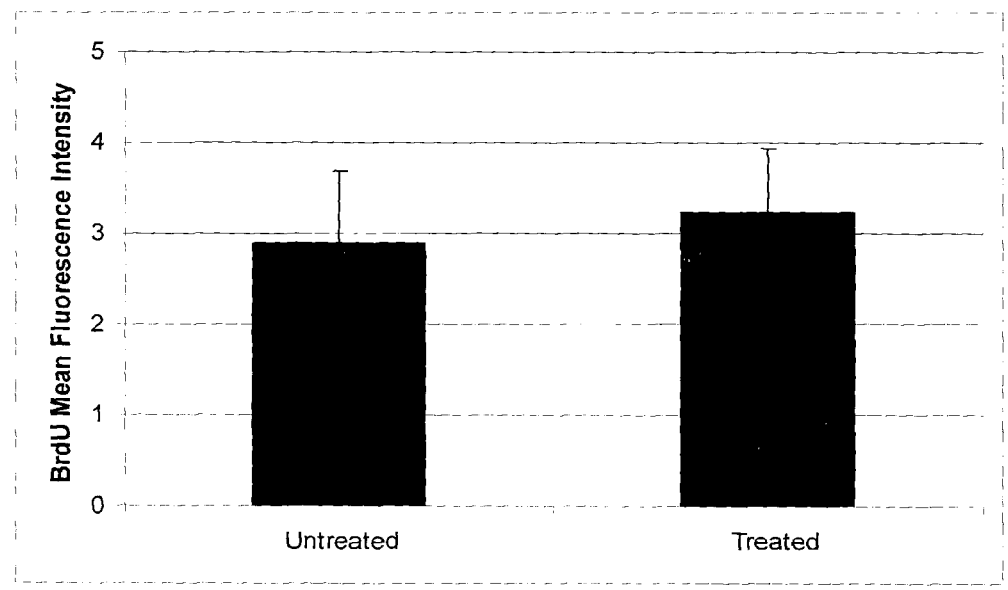

FIG. 2: Proliferation of cells plated in wells treated and untreated with MMC. Proliferation was measured using flow cytometry for BrdU, and quantified using mean fluorescence intensity. There was no significant difference between treated and untreated wells (p=0.62).

Figure 3:
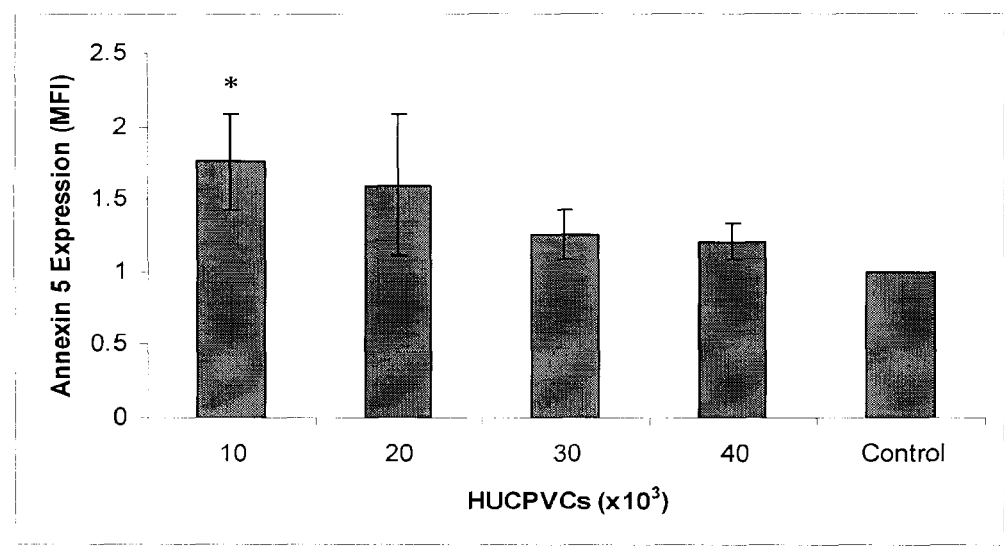

FIG. 3: HUCPVC death was measured using mean fluorescence intensity (MFI) for annexin 5, an early cell death marker, after 4 hours of co-incubation with PBLs from Donor 1 (n=5). There was a significant increase in average annexin 5 expression in the culture with 10% HUCPVCs relative to control (p=0.01, indicated by *); this was the only significant increase.

Figure 4:
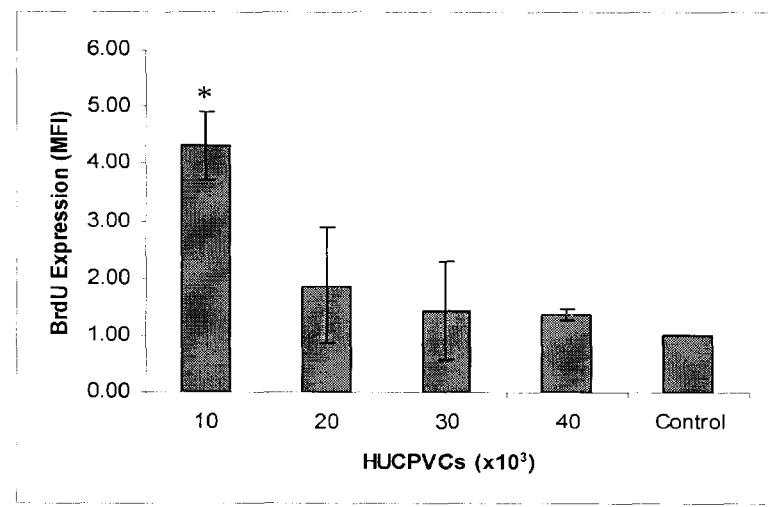

FIG. 4: Lymphocyte proliferation was measured using mean fluorescence intensity (MFI) for BrdU, after 6 days of co-incubation with varying levels of HUCPVCs (n=5). There was a significant increase in average BrdU expression in the culture with 10% HUCPVCs relative to control (p=0.02, indicated by *).

Figure 5:
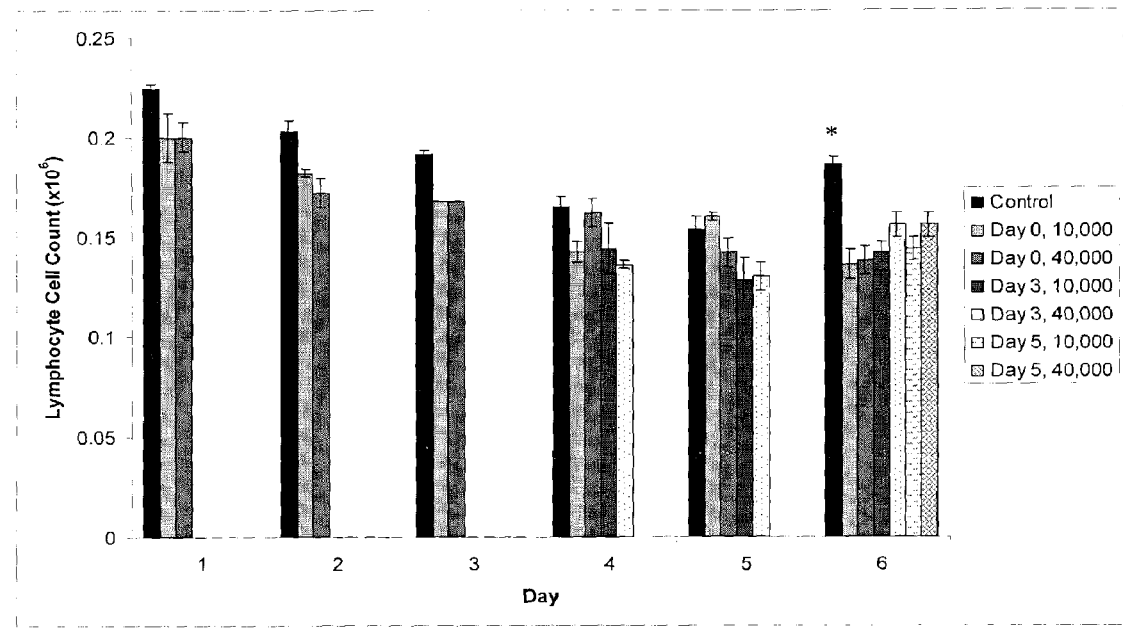

FIG. 5: Total lymphocyte cell number was measured from day 1 to 6 across treatments of 10 and 40% HUCPVCs added on day 0, 3 or 5 (n=3). It can be seen that by day 6, the control lymphocytes have increased in number in response to each other, while the treatments with HUCPVCs were significantly lower regardless of percentage or day added ($p<0.05$, indicated by *).

Figure 6:
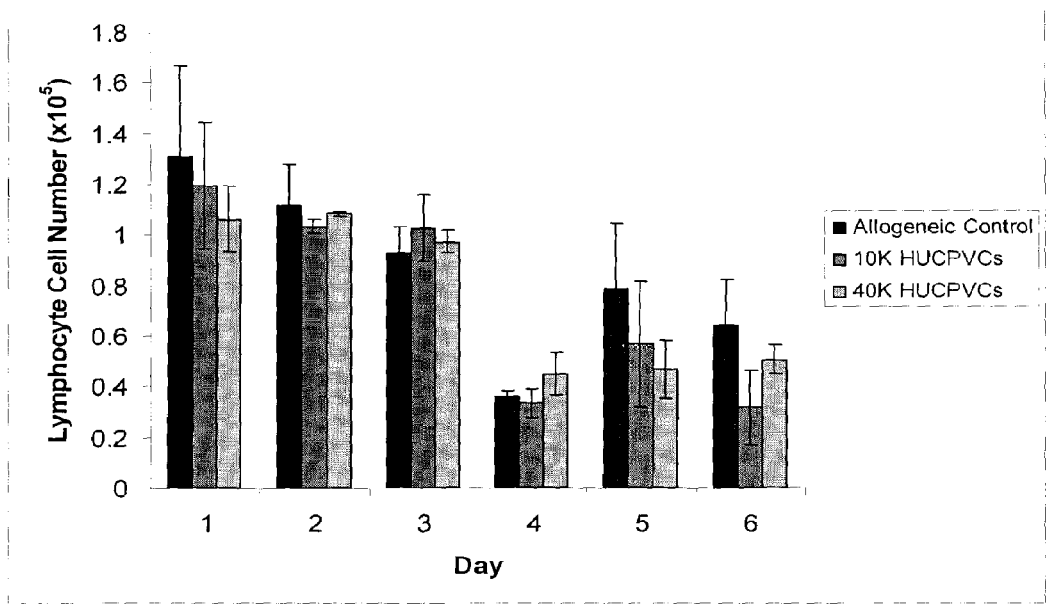

FIG. 6: Total lymphocyte count was measured from day 1 to 6 across treatments of 10 and 40% HUCPVCs added on a TransWell™ insert (n=3). It can be seen that on any day, there is no significant difference between the allogeneic control and the HUCPVC treatments.

Figure 7:
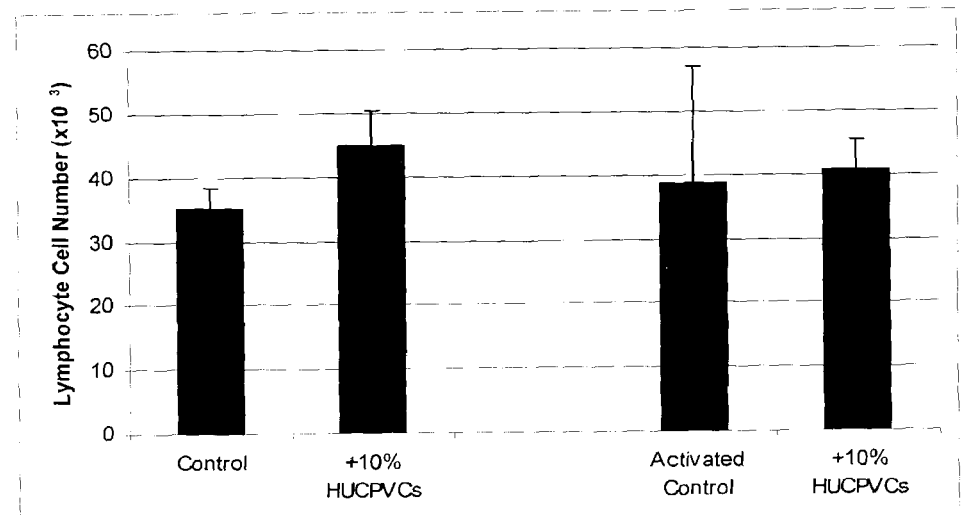

FIG. 7: HUCPVCs do not increase resting or activated lymphocyte cell number. Addition of HUCPVCs showed no significant increase in lymphocyte cell number compared to controls over 6 days in culture (n=6). This Figure shows the average cell numbers, + standard deviations.

Figure 8:
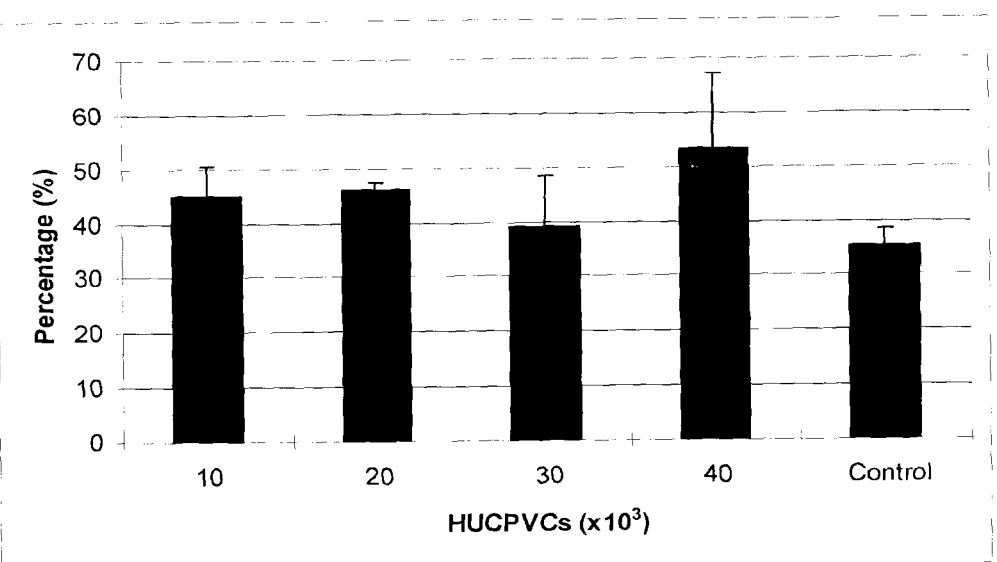

FIG. 8: BrdU expression of PBLs in a co-culture with HUCPVCs measured with flow cytometry. The percentage of cells dividing does not increase with addition of HUCPVCs, irrespective of dose (n=3). Control was the BrdU expression of the PBLs without HUCPVCs.

Figure 9:
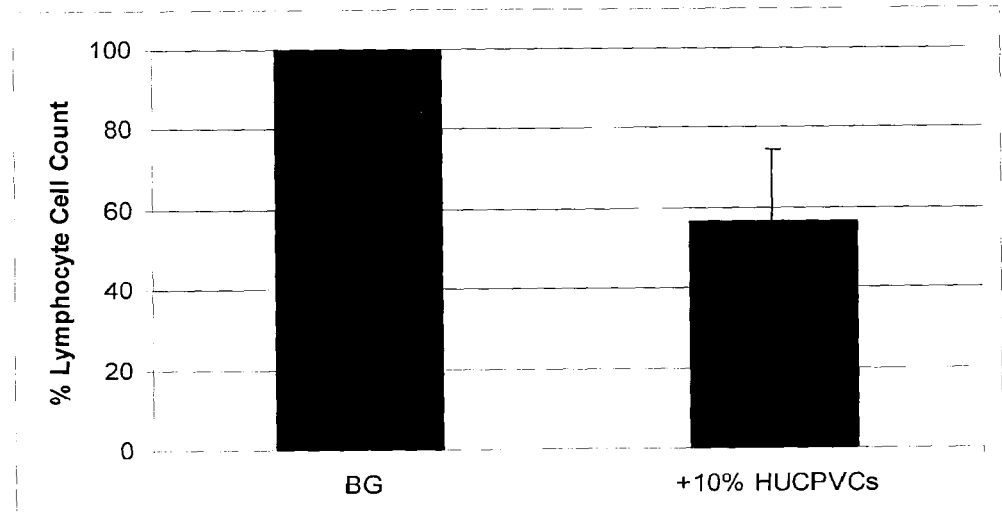

FIG. 9: HUCPVCs act through a soluble factor. HUCPVCs are able to significantly reduce lymphocyte cell number in MLCs, when separated using a TransWell insert. The average control lymphocyte cell number has been set to 100% in the Figure to reduce the variation in counts between experiments.

This figure shows average percentage lymphocyte cell counts, + standard deviation (n=6). (p*<0.05)

Figure 10:
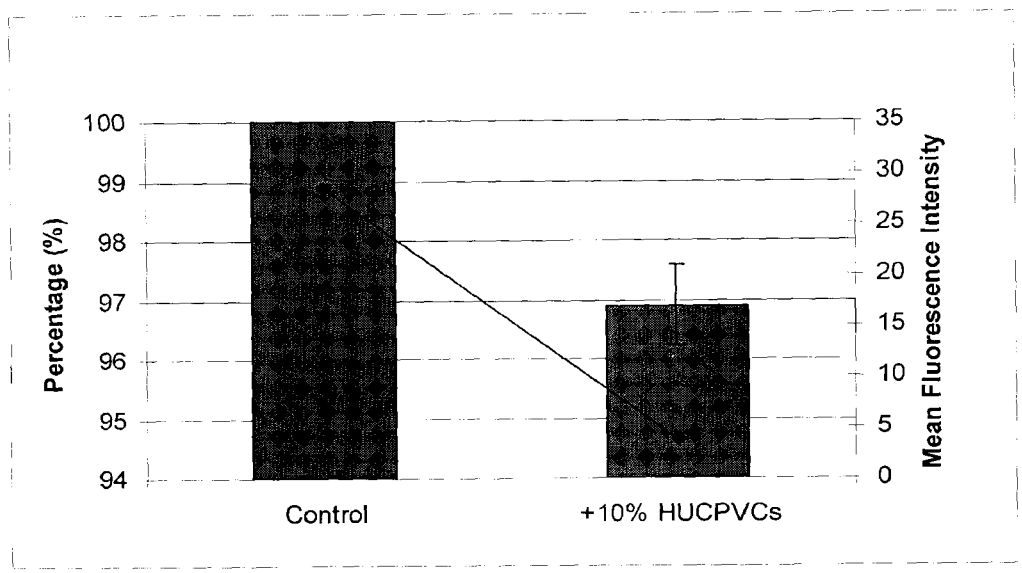

FIG. 10: HUCPVCs reduce CD25 expression in co-cultures of activated lymphocytes. This Figure illustrates both the average percentage expression (bar) and mean fluorescence intensity (line) of CD25 expression on lymphocytes co-cultured with and without 10% HUCPVCs. Lymphocytes were stained with PKH26 to ensure proper detection of the population, and results are gated on PKH26 expression. Averages are + standard deviations (n=3). (*p<0.05)

Figure 11:
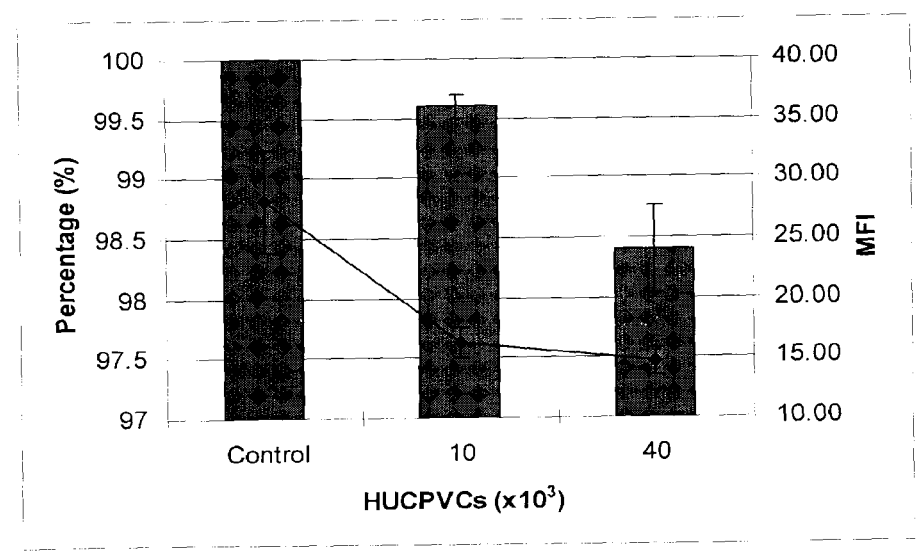

FIG. 11: CD45 expression in a two-way MLC (with activated lymphocytes) with HUCPVCs. The activated lymphocytes were stained with PKH26 to delineate them from the inactive population, and results are gated on PKH26 expression. Both percentage expression (bar*p<0.05) and MFI (line+p<0.05) are shown (n=3). Control was the CD45 expression of the ATL with no HUCPVCs.

Figure 12:
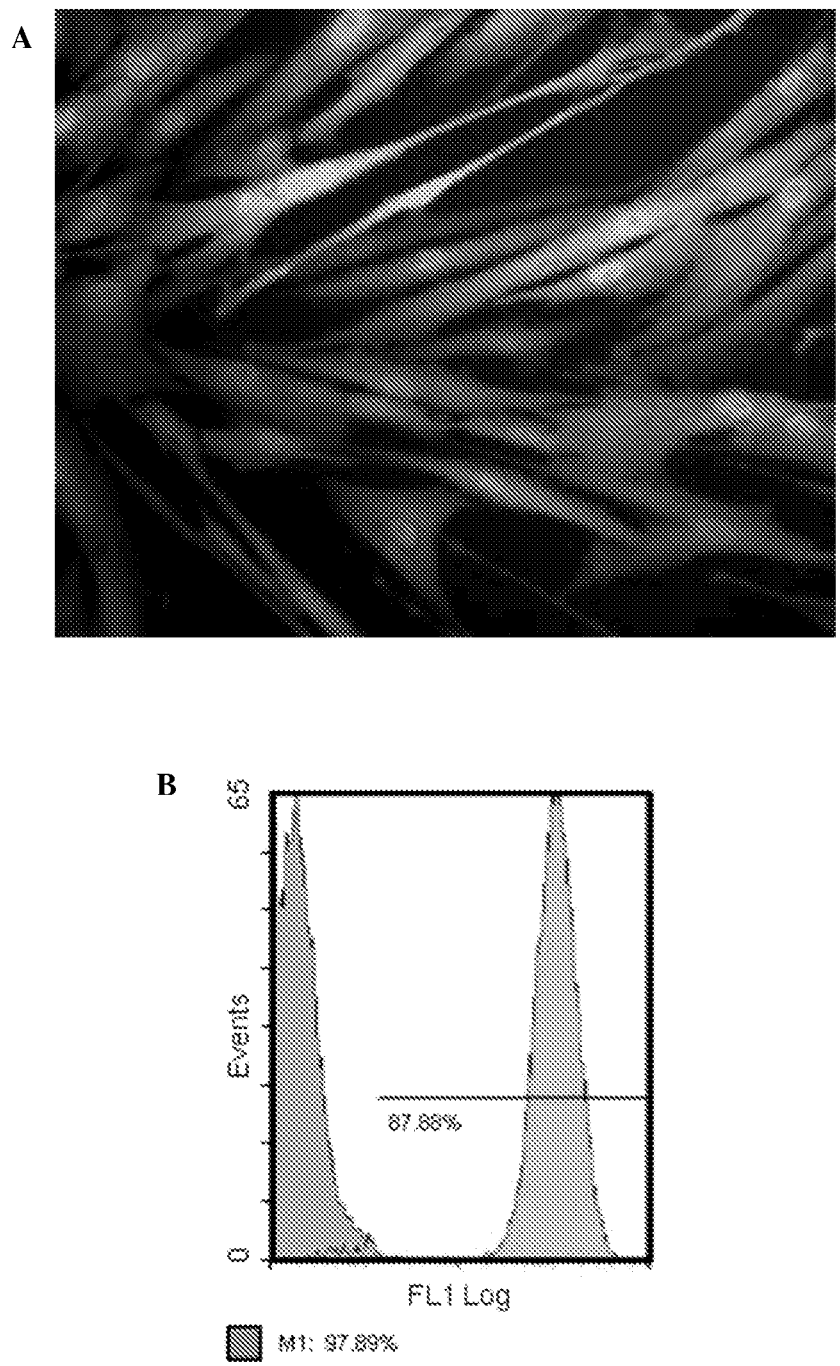

FIG. 12: (A) HUCPVCs transfected with Green Fluorescent Protein (GFP), with an expression level of 97.89% (B). These cells were transfected with a lentiviral vector, using established techniques, and FIG. 13: High-throughput Cancer Pathfinder Gene Array results for bone marrow-derived MSCs (A) and HUCPVCs (B). Genes in parentheses represent those genes which are absent.

DETAILED DESCRIPTION AND PREFERRED EMBODIMENTS

The present invention provides novel and clinically useful applications of HUCPVCs, particularly in the treatment of conditions that would benefit from a reduction in the adverse response elicited by alloantigenic and xenoantigenic bodies, resulting either from an adverse immune response by the host, or from an adverse immune reaction by the antigenic body to the host. More generally, the present invention provides a method in which HUCPVCs and/or soluble factors produced by them are introduced to inhibit or reduce immune reactions between lymphocytes and bodies recognized as foreign.

As used herein, such bodies can include any living or dead biological material that is delivered to or invasive to the body of a mammal, including a human. Antigenic such bodies are those which in the normal course elicit an immune response either by the recipient or by the body, for instance where the body itself comprises immune cells including lymphocytes, such as a bone marrow, tissue or organ graft. Alloantigenic bodies are bodies that are antigenic between individuals within the same species; xenoantigenic bodies are antigenic between individuals of different species. Autologous bodies are bodies from the recipient. In embodiments, the bodies are HLA mismatched bodies. In other embodiments, the bodies comprise HLA mismatched lymphocytes.

While the mechanism of HUCPVC immunomodulatory action is not completely understood, it is expected that the HUCPVCs and soluble factors produced by them have an effect on the major cell populations involved in alloantigen recognition and elimination, such as antigen presenting cells, T cells including cytotoxic T cells, and natural killer cells.

The HUCPVCs useful in the present method are described in the literature, as noted hereinabove, and are characterized more particularly as progenitor cells extractable from the perivascular region of umbilical cord, including but not limited to human umbilical cord. Using the protocol described herein, it will be appreciated that umbilical cord perivascular cells can also be extracted from the umbilical cord vasculature of other mammals, including horses, cows, pigs, primates and the like. The perivascular region comprises the Wharton's jelly associated with and external of the umbilical cord vasculature. The HUCPVCs are extractable from the Wharton's jelly that lies in the perivascular region, using standard methods of digestion such as with collagenase or related enzymes suitable for removing associated connective tissue, as described for instance by Sarugaser et al, 2005, the entire contents of which are incorporated herein by reference. Preferably, HUCPVCs are harvested only from the perivascular cells, and not from Wharton's jelly extending beyond the perivascular region, or from tissues or fluids that are part of or internal to the vasculature itself. This avoids contamination by other cells within the cord generally. In the alternative, extraction from the Wharton's jelly without selection for perivascular cells can be performed, provided the resulting cell population is enriched for HUCPVCs using for instance flow cytometry to enrich for progenitor cells having the phenotype and characteristics noted herein. The HUCPVCs further are characterized by relatively rapid proliferation, exhibiting a doubling time, in each of passages 2-7, of about 20 hours (serum dependent) when cultured under standard adherent conditions. Phenotypically, the HUCPVCs are characterized, at harvest, as Oct 4-, CD14-, CD19-, CD34-, CD44+, CD45-, CD49e+, CD90+, CD105(SH2)+, CD73 (SH3)+, CD79b-, HLA-G-, CXCR4+, c-kit+. In addition HUCPVCs contain cells which are positive for CK8, CK18, CK19, PD-L2, CD 146 and 3G5 (a pericyte marker), at levels higher than in cell populations extracted from Wharton's jelly sources other than the perivascular region.

HUCPVCs can also express variable levels of MHC class I, from 0-100% dependent upon manipulation. By subjecting harvested cells to a freeze-thaw cycle, as described for instance by Sarugaser et ah, 2005, incorporated herein by reference, one obtains a HUCPVC population that is substantially negative for both MHC class I and MHC class II (95%). As used herein, the HUCPVCs are considered to be "substantially" negative for MHC class I and MHC class II if the number of cells resident in a given population and expressing either one or both phenotypes is not more than about 20% of the cell population, e.g., not more than 15%, 10%, 5% or less of the total HUCPVC population. A determination can be made using standard techniques of flow cytometry with appropriate tagged antibody. This MHC double negative HUCPVC population is particularly useful in the methods of the present invention. It will be appreciated that, in the present method, the administered HUCPVC population can comprise either freshly extracted (optionally expanded) MHC class I negative cells, or the thawed MHC double negative HUCPVCs. The MHC double negative HUCPVCs are far less likely to stimulate an immune response in a recipient, and their clinical use is accordingly preferred herein. It should be appreciated, however, that manipulation of the MHC phenotype is not essential. The immunoprivilege and immunomodulation properties are seen also in freshly extracted HUCPVCs that have optionally been stored, and not only in HUCPVCs that have been manipulated by freeze/thaw.

In the present method, HUCPVCs are exploited for their immunoprivileged and immunomodulatory properties, in clinical setting that would benefit therefrom. The term "immunoprivileged" is used herein with reference to cells, such as HUCPVCs, that when incubated with peripheral blood lymphocytes, either do not stimulate PBL proliferation to a statistically significant extent, or retain their viability at a statistically significant level, particularly when tested using the so-called one-way MLC assay established in this art and exemplified herein.

The term "immunomodulatory" is used herein with reference to the ability of HUCPVCs to mitigate, reduce or inhibit the reaction between mismatched populations of lymphocytes, as revealed either by a reduction in the mortality of a lymphocyte population, or by an increase in the viability of a lymphocyte population, as determined using, for instance, the so-called one- or two-way mixed lymphocyte reaction (MLR).

It has in addition been found that factors exuded by cultured HUCPVCs can alone exert an immunomodulatory effect, of the type seen when intact HUCPVCs are used. Thus, in aspects and embodiments of the present invention, the extracted soluble factors produced upon culturing of HUCPVCs are used either alone or in combination with the HUCPV cells, as immunomodulators.

The one or more immunomodulatory factors exuded upon HUCPVC culturing are referred to herein a soluble factors, and are extractable from the medium in which HUCPVCs are cultured. In one embodiment, the immunomodulating soluble factors are provided as an extract obtained when HUCPVC cells are removed from the medium conditioned by their growth, such as by centrifugation. When centrifugation is employed, the extract is provided as the supernatant. Suitable HUCPVC culturing conditions are exemplified herein. The extract is obtained by separating the cells from the conditioned culturing medium, such as by centrifugation. In other embodiments, the soluble factors are provided as an immunomodulating fraction of such extract. An extract fraction having immunomodulating activity is also useful herein, and can be identified using the mixed lymphocyte reactions described herein. These extract fractions can of course be obtained by fractionating the HUCPVC extract using any convenient technique including solvent extraction, HPLC fractionation, centrifugation, size exclusion, salt or osmotic gradient fractionation and the like. Eluted or collected fractions can then each be subjected to the MLR and fractions active for immunomodulation can be identified, and a fraction with immunomodulating activity can be used clinically in the manner described herein.

Thus, in embodiments, the present invention comprises the use of immunomodulating extracts or immunomodulating fractions thereof comprising soluble factors exuded during culturing of HUCPVCs.

Use of the HUCPVCs, and populations thereof that are immunoprivileged and/or immunomodulatory, in accordance with the present invention, entails their collection, optionally their expansion, further optionally their cryogenic storage and revival from the frozen state, and their subsequent formulation for administration to the intended recipient. The particular manipulation, dosing and treatment regimen will of course depend on numerous factors, including the type and severity of the disease or condition to be treated. For immunological conditions (eg. GvHD, autoimmune conditions), the size of the HUCPVC population, i.e., the dose administered to the recipient, will lie generally in the range from 0.01 to about 5 million cells per kilogram of recipient body weight. For delivery, the cells are provided suitably as a formulation further comprising a physiologically tolerable vehicle, i.e., a vehicle that is tolerable not only by the cells but also by the recipient. Suitably, the cells are provided in a sterile formulation comprising, as carrier, a physiologically tolerable vehicle such as saline, buffered saline such as PBS, cell culture medium or similar liquid containing any of: essential amino acids, growth factors, cytokines, vitamins, antibiotics or serum-free chemically defined media etc, or sterile water. The formulated cells can be administered by infusion, or by injection using for instance volumes in the 1-25 mL range.

The immunomodulating soluble factors produced by HUCPVC and extractable from spent HUCPVC culturing medium are similarly useful in the manner described above with reference to intact HUCPVCs. In one embodiment, the extract itself constitutes the pharmaceutical composition, thus comprising the active agent in the form of immunomodulating soluble factor, and the medium constituting the physiologically tolerable vehicle. In the alternative, the extract can be dried, to retain the soluble factor(s) and reconstituted in a different vehicle, such as phosphate buffered saline. The dosage size and dosing regimen suitable for clinical applications can be determined with reference to the dosing effective for intact HUCPVCs. The dose equivalent of extract can be determined by calculating the relative potencies of the extract and intact cells in the MLR assay, or any alternative thereto which is reflective of the clinical environment in which the therapy will be exploited, such as in appropriate animal models of the targeted indication.

In use, the formulated HUCPVCs or soluble factors produced thereby are administered to treat subjects experiencing or at risk of developing an adverse immune reaction. Such subjects include particularly subjects receiving or about to receive an allogeneic or xenogenic transplant or graft, in the form of cells such as marrow and peripheral blood, tissues including skin and vascular tissue including coronary tissue and gastrointestinal tissue, or an organ such as liver, kidney, heart, lung, etc. The formulated HUCPVCs are useful particularly to reduce the onset or severity of graft versus host disease, a condition resulting from an immune attack of host tissues mediated by lymphocytes present in the donor graft. In one embodiment of the invention, the HUCPVCs can be used to treat the graft by incubation therewith for a period of time, prior to transplantation, sufficient to reduce or arrest the activity of lymphocytes resident in the graft. This incubation would require HUCPVCs (from either fresh or frozen stock) to be included at a dose of 5-60% of total graft lymphocytes (as determined by the volume of blood present in the graft), preferably 10-40% for between 4 and 10 days, in order to halt proliferation prior to implantation. In the case of an organ graft, the organ would be incubated with HUCPVCs (suspended in a physiologically tolerable vehicle as mentioned above), from either fresh or frozen stock, at a dose of 0.01 to $5 \times 10^3$ cells per gram mass of the organ, prior to implantation, for a period of time to cause the organ's lymphocytes to become inactive. For subjects that are graft recipients, the HUCPVCs desirably are administered by in the tissue directly surrounding the allogeneic organ to the recipient prior to (e.g. within hours of), concurrently with, or after grafting (e.g., within hours after, and thereafter as necessary to control immune reaction). The HUCPVCs can be administered, most suitably at the site of the graft, such as by infusion or injection, either subcutaneously, intramuscularly, intravasculary, intravenously, intraarterially, or intraperitoneally. In one embodiment, the recipient is treated at the time of grafting by infusion with HUCPVC doses in the range from $5 \times 10^4$ to $5 \times 10^7$ cells per kg body weight, such as about 1 to $5 \times 10^6$ cells. The cells are formulated in 10 ml of normal saline with 5% human serum albumin. Two or more infusions can be used, each lasting about 10-15 minutes. The cells can also be implanted in a slow release formulation that allows the release of viable cells over time at the implantation site (such as intraperitoneal, intramuscular etc). Carriers suitable for this purpose include gelatin, hyaluronic acid, alginate and the like. In another embodiment of the invention, HUCPVCs can be utilized to treat immunological conditions such as GvHD which are underway, and possibly refractory to other treatments. The HUCPVCs or the exuded soluble factors thus will be useful to treat subjects afflicted with leukemias, aplastic anemias and enzyme or immune deficiencies for whom the transplantation of immune cells or tissues containing them are indicated.

The administration of HUCPVCs or the soluble factors also has application in treating autoimmune diseases such as Crohn's disease, lupus and multiple sclerosis, as well as rheumatoid arthritis, type-1 insulin-dependent diabetes mellitus, adult respiratory distress syndrome, inflammatory bowel disease, dermatitis, meningitis, thrombotic thrombocytopernic purpura, Sjogren's syndrome, encephalitis, uveitis, leukocyte adhesion deficiency, rheumatic fever, Reiter's syndrome, psoriatic arthritis, progressive systemic sclerosis, primary biliary cirrhosis, myasthenia gravis, lupus erythematosus, vasculitis, pernicious anemia, antigen-antibody complex mediated diseases, Reynard's syndrome, glomerulonephritis, chronic active hepatitis, celiac disease, autoimmune complications of AIDS, ankylosing spondylitis and Addison's disease. The administration of HUCPVCs in this case is intravenously in a physiologically tolerable vehicle (as mentioned previously), with a dose ranging from $0.1\text{-}10 \times 10^6$ cells/kg body weight. More than one dose may be required, and dosing can be repeated as needed.

Secondly, HUCPVCs can be used to treat protein/enzyme deficiencies, wherein the HUCPVCs have been transfected with the gene necessary to produce the desired protein/enzyme. This process can include transduction (including but not limited to: lentiviral, retroviral and adenoviral); and transfection (including but not limited to: nucleofection, electroporation, liposomal) and are transfused into a patient suffering from a deficiency. The dose administered to the recipient will lie generally in the range from 0.01 to about 5 million cells per kilogram of recipient body weight. HUCPVCs will then produce the protein or enzyme of interest constitutively Finally, HUCPVCs can be engineered to introduce transgenes, via the transfection methods mentioned above, for use as vaccines in order to generate large quantities for administration to people at risk of exposure to specific viruses/antigens.

MATERIALS AND METHODS

Cell Harvests
HUCPVCs

Ethical consent for this research was obtained from the University of Toronto as well as Sunnybrook & Women's College Health Sciences Centre. Umbilical cords were collected from aseptic caesarean births of full term babies, upon obtaining informed consent from both parents. The cords were immediately transported to the University of Toronto where cells were extracted from the perivascular area under sterile conditions as reported previously[16]. Briefly, 4 cm sections of cord were cut, and the epithelium was removed. The vessels were then extracted including their surrounding Wharton's jelly, tied in a loop to prevent smooth muscle digestion, and digested overnight in a collagenase solution. Upon removal from the digest the following day, the cells were rinsed in ammonium chloride to lyse any red blood cells from the cord blood. Following this, the cells were rinsed and plated out in 85% α-MEM containing 5% fetal bovine serum and 10% antibiotics (penicillin G at 167 units/ml; Sigma, gentamicin 50 µg/ml; Sigma, and amphotericin B 0.3 µg/ml) at a density of 4,000 cells/cm$^2$. The cells are passaged when they reach 75-80% confluence, which is approximately every 6-7 days.

MHC−/− HUCPVCs

Test cell populations of $>1 \times 10^5$ cells were washed in PBS containing 2% FBS and re-suspended in PBS+2% FBS with saturating concentrations (1:100 dilution) of the following conjugated mouse IgG1 HLA-A,B,C-PE (BD Biosciences #555553, Lot M076246) (MHC I), HLA-DR,DP,DQ-FITC (BD Biosciences #555558, Lot M074842) (MHC II) and CD45-Cy-Cychrome (BD Biosciences #555484, Lot 0000035746) for 30 minutes at 4° C. The cell suspension was washed twice with PBS+2% FBS and re-suspended in PBS+ 2% FBS for analysis on a flow cytometer (XL, Beckman-Coulter, Miami, Fla.) using the ExpoADCXL4 software (Beckman-Coulter). Positive staining was defined as the emission of a fluorescence signal that exceeded levels obtained by >99% of cells from the control population stained with matched isotype antibodies (FITC-, PE-, and Cy-cychrome-conjugated mouse IgG1, κ monoclonal isotype standards, BD Biosciences), which was confirmed by positive fluorescence of human BM samples. For each sample, at least 10,000 list mode events were collected. All plots were generated in EXPO 32 ADC Analysis software.

The attached cells were sub-cultured (passaged) using 0.1% trypsin solution after 7 days, at which point they exhibited 80-90% confluency as observed by light microscopy. Upon passage, the cells were observed by flow cytometry for expression of MHC-A,B,C, MHC-DR,DP,DQ, and CD45. They were then plated in T-75 tissue culture polystyrene flasks at $4 \times 10^3$ cells/cm$^2$ in SM, and treated with $10^{-8}$ M Dex, 5 mM β-GP and 50 µg/ml ascorbic acid to test the osteogenic capacity of these cells. These flasks were observed on days 2, 3, 4, 5 and 6 of culture for CFU-O, or bone nodule, formation. Any residual cells from the passaging procedure also were cryopreserved for future use.

Aliquots of $1 \times 10^6$ PVT cells were prepared in 1 ml total volume consisting of 90% FBS, 10% dimethyl sulphoxide (DMSO) (Sigma D-2650, Lot#11K2320), and pipetted into 1 ml polypropylene cryo-vials. The vials were placed into a −70° C. freezer overnight, and transferred the following day to a −150° C. freezer for long-term storage. After one week of cryo-preservation, the PVT cells were thawed and observed by flow cytometry for expression of MHC-A,B,C, MHC-DR, DP,DQ, and CD45. A second protocol was used in which the PVT cells were thawed after one week of cryopreservation, recultured for one week, sub-cultured then reanalyzed by flow cytometry for expression of MHC-A,B,C, MHC-DR, DP,DQ, and CD45.

It was noted that the frequency of MHC−/− within the fresh cell population is maintained through several passages. When fresh cells are frozen after passaging, at −150° C. for one week and then immediately analyzed for MHC phenotype, this analyzed population displays a remarkably enhanced frequency of cells of the MHC−/− phenotype. In particular, first passage of cryopreserved cells increases the relative population of MHC−/− cells to greater than 50% and subsequent freezing and passaging of those cells yields an MHC−/− population of greater than 80%, 85%, 90% and 95%.

Lymphocytes

Peripheral blood lymphocytes (PBLs) were extracted from heparinized blood from healthy donors. Cell separation was achieved by Ficoll-Paque™ PLUS density gradient (Amersham Biosciences #17-1440-03) in which the cells were spun for 35 minutes at 380×g. The buffy coat was removed and counted using a ViCell-XR™ (Beckman Coulter) with a protocol specific for lymphocytes as determined by cell and nucleus size. The cells were then plated out as per the requirements of the assay in 80% RPMI-1640 media (Sigma

R5886) containing HEPES (25 mmol/L), L-Glutamine (2 mmol/L), 10% fetal bovine serum and 10% antibiotics.

Mixed Lymphocyte Cultures

Mitomycin C

In order for one-way MLCs to be performed, the HUCPVCs and one of the PBL populations have to remain quiescent. This is achieved by treating the cells with mitomycin C (MMC) at a set concentration and time, allowing the MMC to adhere to the DNA and prevent division. This concentration was determined by a titration curve of MMC incubated for 20 minutes at 37° C. (5% $CO_2$) with a starting cell population of 5000 cells in a well of a 96 well plate. Concentrations of 10, 20, 30, 40, 50, and 75 µg/mL of MMC were tested in regular media (85% α-MEM, 5% FBS, 10% antibiotics) and washed twice with PBS afterwards to remove any traces of the MMC. The wells were counted after a week to assess proliferation. It is essential that all traces of MMC are removed so it does not affect the proliferative capacity of lymphocytes when the cell populations are combined in an MLC. To ensure this, empty wells of a 96 well plate (Falcon) were treated with MMC and washed as per the protocol. Lymphocytes were then added and assayed for their proliferation compared to control normal wells.

Imunoprivilege Assays

Triplicates of $1\times10^4$ HUCPVCs (both fresh and frozen have been assayed) were plated in 96 well plates (n=5). Once the cells had attached (after approximately 2 hours), they were treated with MMC at 20 µg/mL. The HUCPVCs were then rinsed, and $10^5$ PBLs from Donor 1 were added to each well. The plates were incubated at 37° C. with 5% $CO_2$ air in 80% RPMI-1640 media containing HEPES (25 mmol/L), L-Glutamine (2 mmol/L), 10% fetal bovine serum and 10% antibiotics. After 6 days the lymphocytes present in culture with HUCPVCs were counted using the ViCell counter, and compared to controls. For the cell death assay, plates were allowed to incubate for four hours, and HUCPVCs were assessed for early and late stage cell death markers; annexin 5 (R&D Systems TA4638) and 7-amino-actinomycin D (7-AAD) respectively. These levels were measured and compared using Flow Cytometry on a Beckman Coulter FlowCenter. For the PBL proliferation assay, the cells were allowed to incubate for 6 days, after which they were stained with 5-bromo-2-deoxyuridine (BrdU), a base analog of thymidine, and measured using flow cytometry. Controls of PBLs alone and HUCPVCs alone were used for both assays.

For one-way MLCs, HUCPVCs were first plated in a 96 well plate in triplicate (1, 2, 3, and $4\times10^4$ cells per well), treated with MMC and washed with PBS. PBLs were retrieved from two unmatched donors selected from a pool of potential donors (Mismatch on 5 out of 6 HLA tested: Donor 1 HLA-A*01, *02; B*07, *18; DRB1*15, *—; Donor 2 A *01, *—; B*08, *—; DRB1 *03, *—). Typing was performed at the Regional Histocompatibility Laboratory (Toronto General Hospital, Toronto, ON) using DNA assignment techniques at low resolution. After Ficolling, Donor 2's lymphocytes were treated with MMC to be quiescent. The cells were then spun down and washed, and added to a 96 well plate at $10^5$ cells per well. Donor 1's lymphocytes were added at $10^5$ cells per well and the three cell populations were allowed to co-incubate for 6 days, after which they were stained with 5-bromo-2-deoxyuridine (BrdU), a base analog of thymidine. Flow cytometry for BrdU was then performed on the lymphocytes to assay proliferation. Following this, a similar assay was performed with the result being measured using daily counts of lymphocytes (from day 1 to 6) using the ViCell-XR™ cell counter, with a lymphocyte-specific protocol. All results were compared to allogeneic and autologous controls from both donors.

Immunomodulation Assays

Two-way MLCs incorporate two PBL populations from unmatched donors (same donors as above), both of which are permitted to proliferate. Briefly, $1\times10^5$ PBLs from both donors were added to each well of a 96 well plate and left to incubate for six days. In the course of the experiment, either 1 or $4\times10^4$ HUCPVCs were added to wells in triplicate on days 0, three or five in order to analyze the effectiveness of HUCPVCs if an immune reaction has already begun. The 10 and 40% HUCPVC:PBL ratios were chosen as both had showed positive results previously, and thus were chosen as the low and high levels of HUCPVC inclusion. Samples from each plate were counted every day using the ViCell-XR™ cell counter and compared to autologous and allogeneic controls.

Soluble Factor

The two-way MLC assay was performed again, without direct HUCPVC to PBL cell contact to determine if the effect noted was due to a soluble factor, or if cell-cell contact was necessary. The HUCPVCs (1 and $4\times10^4$ cells per well) were cultured on a Transwell® insert (Corning) for a 24 well plate, and allowed to attach for approximately 2 hours. Once they had attached, the insert was transferred to the 24 well plate that contained a co-culture of PBL populations from Donor 1/Donor 2 (same donors as above) (n=3). The lymphocyte cell numbers were counted daily for six days and compared to autologous and allogeneic controls using the ViCell-XR™.

Lymphocyte Activation

Both immunoprivilege assays and two-way MLCs were performed as mentioned previously. The endpoint of this assay was flow cytometric analysis of the lymphocytes for the presence of IL-2R (CD25) (Becton Dickinson, #555431), a marker of activated lymphocytes. This assay was performed over 6 days to determine if HUCPVCs caused an increase or decrease in lymphocyte activation. Lymphocytes were also co-stained with CD45 to ensure proper cell population was obtained. Negative controls were lymphocyte cultures with no HUCPVCs added, and unstained.

Activated T Cell Line Generation

PBLs were extracted from Donor 1 and 2 as previously, and separated using the Ficoll gradient. The cells were counted, and cells from Donor 2 were rendered quiescent with MMC. $10^6$ Cells from Donor 1 were plated in a 24 well plate, and stimulated with a 1:1 ratio of quiescent PBLs from Donor 2. The cells were fed with 2 mLs of RPMI-1640 media (supplemented with 10% serum and 10% supplements as previously) and allowed to activate. Media was changed upon a perceptible change of its colour to yellow (~3 days). After ~11 days (or when the media changed colour in under 3 days), the cells were harvested and counted. They were re-plated at $10^6$ per well, and re-stimulated with a 1:1 ratio of quiescent PBLs from Donor 2. Upon the second stimulation, IL-2 was added at a concentration of 100 U/mL (BD Biosciences #354043), every 2 days with feeding. When media turned yellow before 3 days, the cells were harvested, counted and split. Following this procedure, the cells were ready to be used as Activated T lymphocytes (ATLs), with specific antibodies to Donor 2. The PBL co-culture and two-way MLCs were carried out as previously and assayed for cell proliferation and expression of CD25.

Lymphocyte Labelling

In order to visualize, and quantify, the difference between two lymphocyte populations, PKH26 was used (Sigma #PKH26-GL). PHK26 is a non-cytotoxic membrane dye with a long half life (~100 days). Cells were stained as per the protocol supplied with the product: lymphocytes were trypsinized, pooled, and pelleted; the diluted dye was then added to the cell suspension for 2 to 5 minutes (2 mL of $2\times10^{-6}$ molar PHK26 solution). After staining, an equal volume of serum was added to halt the reaction; the cells were suspended in media, spun down and washed several times. The stain was then visualized on the fluorescence microscope to ensure appropriate dye uptake resulted. The cells used for staining were the ATLs obtained from Donor 1; these red cells were included in an MLC with unstained cells from Donor 2, and HUCPVCs. The endpoint of the assay was flow cytometry for CD45 (BD #555482) and CD25, gated on the presence or absence of PKH26. Negative controls were unstained cells, and MLCs with no HUCPVCs Transfection First, 293 Cells are transfected with the desired DNA and plasmids (vector DNA, 10 μg gag/pol expressing plasmid, 10 μg of rev expressing plasmid, 10 μg of tat expressing plasmid, 5 μg of VSV-G expressing plasmid with 2.5 M $CaCl_2$). These are allowed to incubate overnight, after which the media is changed. Cells are then left with this media for three more days, after which the supernatant of the cells is collected and filtered. The viral supernatant is then concentrated with ultracentrifugation (50000 g for 90 minutes) or using an Amicon Ultra-15 Centrifugal Filter device (100,000 MWCO; Millipore). When this process is complete, the viral supernatant can be combined with the HUCPVCs at a concentration determined by titering the concentrated virus, and allowed to incubate overnight. The following day, more media is added, and the cells incubate for 6 more hours before changing the media. In this manner, HUCPVCs can be engineered to introduce and express a transgene that encodes any protein, including proteins useful to manage adverse immune reactions (immunosuppressive proteins). Such proteins include CTLA4, VCP, PLIF, LSF-1, Nip, CD200 and Uromodulin.

Microarray Analysis

The Oligo GEArray Human Cancer Microarray (Superarray Biosciences, Frederick Md., Cat#: OHS-802) was used to find changes in the expression of genes representative of several different pathways frequently altered during the progression of cancer The Oligo GEArray for human cancer has 440 representative cancer genes and is organized into functional gene groupings including apoptosis, cell cycle, cell growth and differentiation, signal transduction, and other cancer-related genes.

HUCPVCs and human bone marrow-derived MSCs were grown to passage 2 and RNA was isolated from these cells. Purified RNA was processed according to manufacturer's protocol (Superarray Biosciences Corp.) and hybridized to Oligo GEArray Human Cancer microarrays. The Oligo GEArray Human Cancer Microarray was used to determine the differential expression of genes related to cancer in HUCPVCs compared with normal human bone marrow-derived MSCs.

RESULTS

Mitomycin C is an Effective Antiproliferative Agent on HUCPVCs

HUCPVCs were treated with a range of concentrations of MMC for 20 minutes at 37° C. (5% $CO_2$). FIG. 1 shows the cell numbers of HUCPVCs after one week in culture post-MMC treatment (n=2). All cells show a marked decrease in proliferation relative to control (p<0.001), with no difference among treatments. Thus, 20 μg/mL was chosen in accordance with the literature. FIG. 2 illustrates the lack of effect of cells plated in wells treated with MMC and washed, versus untreated wells (n=2, p=0.16). Therefore, the MMC will not have an effect on experimental results obtained in wells previously treated with MMC. All statistics presented herein were obtained using ANOVAs to compare means via the R Project for Statistical Computing.

HUCPVCs are not Recognized as Foreign by Lymphocytes

Upon co-incubation of a HUCPVC population with lymphocytes (Donor 1), there was a statistically significant increase in HUCPVC death at a proportion of 10% HUCPVC:PBL (n=5, p=0.01), as measured by annexin 5 mean fluorescence intensity (MFI). FIG. 3 shows this increased cell death was not noted at HUCPVC doses higher than 10%, thus at the correct proportion, HUCPVCs are not attacked by unmatched lymphocytes. This was confirmed using a lymphocyte proliferation assay in which it can be seen that lymphocytes do proliferate in response to 10% HUCPVC:PBL, as measured by BrdU MFI (p=0.02), but not at higher HUCPVC concentrations (FIG. 4). Lymphocyte proliferation is a standard measure of activation, as division of both T and B lymphocytes occurs in the activation cascade. Therefore at a lower proportion, HUCPVCs do not provide enough of a presence such that their immunological avoidance capabilities are realized. However at higher concentrations, 20-40%, the PBLs do not proliferate, and the HUCPVCs are not killed.

HUCPVCs were also analyzed for their effect on lymphocyte cell number upon inclusion in a co-culture with resting PBLs or ATLs. In both cases, HUCPVCs caused no significant increase over control cell number (PBL: $35.2\pm3.1\times10^3$, +10% HUCPVCs $45.0\pm5.7\times10^3$; ATL: $38.8\pm18.2\times10^3$, +10% HUCPVCs $40.8\pm4.8\times10^3$), indicating their immunoprivilege in either resting or stimulated conditions (FIG. 7).

HUCPVCs were included in a one-way MLC in proportions of 10, 20, 30 and 40% of the PBL population and assessed for their proliferation by BrdU expression after 6 days. FIG. 8 shows no significant increase in the number of cells proliferating regardless of the proportion of HUCPVCs included.

HUCPVCs Are Immunomodulatory

FIG. 5 shows that on day 6 the allogeneic co-cultured lymphocytes have increased in number, whereas all cultures with HUCPVCs present; regardless of when they were added or the proportion added, have a significantly lower lymphocyte cell count than the control (n=3).

HUCPVCs Can Exert Their Action Through A Soluble Factor

Trans Well® inserts were used to separate HUCPVCs from PBLs in a two-way MLC. No significant reduction in lymphocyte number relative to control was seen within any day with either 10% or 40% HUCPVCs (n=3) (FIG. 6). However, upon increasing the sample number, the addition of 10% HUCPVCs showed a significant reduction in lymphocyte cell number over a 6 day culture period compared to control (MLC: $40.7+32.9\times10^3$ cells, 10% HUCPVCs: $21.3\pm14.7\times10^3$ cells) (FIG. 9). Soluble factor(s) may therefore contribute to HUCPVC immunomodulation, however what that factor(s) is/are and how they affect lymphocytes is still unknown.

HUCPVCs Reduce the Activation State of Lymphocytes

ATLs stained with PKH26 were added in a co-culture with 10% HUCPVCs, and assayed for their expression of CD25 (IL-2 receptor), a marker of lymphocyte activation. Upon inclusion of HUCPVCs, both the percentage of cells expressing CD25 (Control: 100%±0, 10% HUCPVC: 96.9%±0.7), and the mean fluorescence intensity (Control: 28.6±0.1, 10% HUCPVC: 3.76±0.1) was significantly reduced (FIG. 10).

Thus, HUCPVCs have a physical effect on activated lymphocytes, by reducing their activation state.

In addition, HUCPVCs reduced the expression of CD45 of the lymphocytes, both the percentage (Control: 100%±0, 10% HUCPVC: 99.6%±0.1, 40% HUCPVC: 98.4%±0.36) and the mean fluorescence intensity (Control: 28.20±4.24, 10% HUCPVC: 16.33±1.27, 40% HUCPVC: 14.70±1.22) were significantly different (p<0.05) (FIG. 11). These results were unexpected as CD45 is expressed on all lymphocytes. However it has been seen that CD45 is crucial for the development and function of lymphocytes[36], and may be a further indication of the reduced function of the lymphocytes due to the addition of the HUCPVCs.

Transfection

HUCPVCs were successfully transfected with GFP, and the cells expressed high levels of the protein. A transfection efficiency of 97% was achieved (FIG. 12), with maintenance of good proliferative rates. This success rate varies according to the passage at which the cells are transfected. With a functioning transfection protocol, it is thus possible to transfect the cells with any protein and have it constitutively expressed.

Microarray Analysis

HUCPVCs do not express any detectable levels of genes associated with tumorigenesis. The gene array analysis resulted in the absence of functional genes associated with human cancer and expressed genes known to be important, for example, in cell cycle regulation, such as Cyclin D1 (CCND1), CCND2 and CCND3 (FIG. 13).

DISCUSSION

Herein described are the in vitro immunoprivileged and immunomodulatory properties of an MSC population from a source other than bone marrow, the human umbilical cord. HUCPVCs are extracted from the perivascular area of the cord, as this was believed to be the most rapidly proliferating population of cells. Previously, it was shown that endothelial cells from the wall of the umbilical cord vein stimulated lymphocytes in vitro[37]. This is in stark contrast to the results reported, and reinforces the distinct area from which HUCPVCs are retrieved.

HUCPVCs thus are well suited for clinical use particularly, but not only, to reduce the onset and/or severity of graft versus host disease, and to reduce or eliminate graft rejection by the host, and for the treatment of other immune-mediated disorders that would benefit from suppression of a mixed lymphocyte reaction. In addition, when manipulated by transfection to contain the gene of a protein/enzyme of interest, HUCPVCs are able to produce this product constitutively, and would thus be useful in the treatment of any condition in which a protein/enzyme deficiency results in a detrimental effect to the patient, especially as they can be used allogeneically in a mismatched patient without rejection. In addition, HUCPVCs can also be used to generate vaccines of interest after transfection with the necessary gene.

As progenitor cells having the propensity to expand and differentiate over time into various mesenchymal tissues dictated by their growth environment, HUCPVCs like other mesenchymal progenitor or stem cells may carry some risk that their growth and differentiation in vivo will not be controlled. Remarkably, as a further benefit of the use of HUCPVCs clinically, it has been determined that the HUCPVCs exhibit extremely low telomerase activity, an indicator of their propensity for tumorigenesis. Furthermore, it has been determined that HUCPVCs lack many of the genetic markers that are hallmarks of tumorigenesis. Tumorigenesis occurs by mutations that deregulate biological pathways and cause cells to grow and divide unchecked, to avoid apoptosis (programmed cell death), to respond abnormally to growth factors, to receive blood supply (angiogenesis), and to migrate from one location to another (metastasis and invasiveness). Many genes are involved in each of these control mechanisms, and a mutation in any one of them can cause deregulation.

The following references are incorporated hereby by reference in their entirety:

REFERENCE LIST

1. Horwitz, E. et al. Clarification of the nomenclature for MSC: The International Society for Cellular Therapy position statement. *Cytotherapy* 7, 393-395 (2005).
2. Bruder, S. P. et al. Mesenchymal stem cells in osteobiology and applied bone regeneration. *Clin. Orthop. Relat Res* S247-S256 (1998).
3. Quarto, R. et al. Repair of large bone defects with the use of autologous bone marrow stromal cells. *N. Engl. J Med* 344, 385-386 (2001).
4. Krebsbach, P. H., Mankani, M. H., Satomura, K., Kuznetsov, S. A., & Robey, P. G. Repair of craniotomy defects using bone marrow stromal cells. *Transplantation* 66, 1272-1278 (1998).
5. Yoo, J. et al. The chondrogenic potential of human bone marrow derived mesenchymal progenitor cells. *J Bone Joint Surg* 80, 1745-1757 (1998).
6. Worster, A. A. et al. Chondrocyte differentiation of mesenchymal stem cells sequentially exposed to transforming growth factor-beta1 in monolayer and insulin-like growth factor-I in a three-dimensional matrix. *J Orthop. Res* 19, 738-749 (2001).
7. Williams, C. G. et al. In vitro chondrogenesis of bone marrow-derived mesenchymal stem cells in a photopolymerizing hydrogel. *Tissue Eng* 9, 679-688 (2003).
8. Sekiya, I., Larson, B. L., Vuoristo, J. T., Cui, J. G., & Prockop, D J. Adipogenic differentiation of human adult stem cells from bone marrow stroma (MSCs). *J Bone Miner Res* 19, 256-264 (2004).
9. Shi, D., Reinecke, H., Murry, C. E., & Torok-Storb, B. Myogenic fusion of human bone marrow stromal cells, but not hematopoietic cells. *Blood* 104, 290-294 (2004).
10. Caplan, A. I. Mesenchymal stem cells. *J Orthopaedic Res* 9, 641-650 (1991).
11. Caplan, A. I. Review: mesenchymal stem cells: cell-based reconstructive therapy in orthopedics. *Tissue Eng* 11, 1198-1211 (2005).
12. Zuk, P. A. et al. Human adipose tissue is a source of multipotent stem cells. *Mol Biol. Cell* 13, 4279-4295 (2002).
13. Sakaguchi, Y. et al. Suspended cells from trabecular bone by collagenase digestion become virtually identical to mesenchymal stem cells obtained from marrow aspirates. *Blood* 104, 2728-2735 (2004).
14. Campagnoli, C. et al. Identification of mesenchymal stem/progenitor cells in human first-trimester fetal blood, liver, and bone marrow. *Blood* 98, 2396-2402 (2001).
15. Mitchell, J. B. et al. Immunophenotype of human adipose-derived cells: temporal changes in stromal-associated and stem cell-associated markers. *Stem Cells* 24, 376-385 (2006).
16. Sarugaser, R., Lickorish, D., Baksh, D., Hosseini, M. M., & Davies, J. E. Human Umbilical Cord Perivascular (HUCPV) Cells: A Source of Mesenchymal Progenitors. *Stem Cells* 23, 220-229 (2005).

17. Sarugaser, R., Hanoun, L., Kwong, F., Stanford, W. L., & Davies, J. E. Human Umbilical Cord Perivascular Cell (HUCPVC) clones determine mesenchymal stem cell identity. 4th Annual. 2006. International Society for Stem Cell Research. Ref Type: Conference Proceeding 18. Baksh, D., Yao, R., & Tuan, R. Comparison of proliferative and multilineage differentiation potential of human mesenchymal stem cells derived from umbilical cord and bone marrow. *Stem Cells* In Press, (2007).

19. Le Blanc, K. Immunomodulatory effects of fetal and adult mesenchymal stem cells. *Cytotherapy* 5, 485-489 (2003).

20. Le Blanc, K. & Ringden, O. Immunobiology of human mesenchymal stem cells and future use in hematopoietic stem cell transplantation. *Biol. Blood Marrow Transplant.* 11, 321-334 (2005).

21. Bartholomew, A. et al. Mesenchymal stem cells suppress lymphocyte proliferation in vitro and prolong skin graft survival in vivo. *Exp Hematol.* 30, 42-48 (2002).

22. Puissant, B. et al. immunomodulatory effect of human adipose tissue-derived adult stem cells: comparison with bone marrow mesenchymal stem cells. *Br. J Haematol.* 129, 118-129 (2005).

23. Gotherstrom, C. et al. Immunologic properties of human fetal mesenchymal stem cells. *Am J Obslet. Gynecol.* 190, 239-245 (2004).

24. Gotherstrom, C., Ringden, O., Westgren, M., Tammik, C., & Le Blanc, K. Mesenchymal Stem Cells: Immunomodulatory effects of human foetal liver-derived mesenchymal stem cells. *Bone Marrow Transplantation* 32, 265-272 (2003).

25. Le Blanc, K. et al. Treatment of severe acute graft-versus-host disease with third party haploidentical mesenchymal stem cells. *The Lancet* 363, 1439-1441 (2004).

26. Ringden, O. et al. Mesenchymal stem cells for treatment of therapy-resistant graft-versus-host disease. *Transplantation.* 2006. May, 27. 1390-1397 (2006).

27. Taupin, P. OTI-010 Osiris Therapeutics/JCR Pharmaceuticals. *Curr. Opin. Investig. Drugs.* 7, 473-481 (2006).

28. Osiris Therapeutics. Prochymal™ Adult Human Mesenchymal Stem Cells for Treatment of Moderate-to-Severe Crohn's Disease. NCT00294112. 2006. www.clinicaltrials.gov.
Ref Type: Report 29. Le Blanc, K. et al. Fetal mesenchymal stem-cell engraftment in bone after in utero transplantation in a patient with severe osteogenesis imperfecta. *Transplantation* 79, 1607-1614 (2005).

30. Liu, H. et al. The immunogenicity and immunomodulatory function of osteogenic cells differentiated from mesenchymal stem cells. *J Immunol.* 176, 2864-2871 (2006).

31. Eliopoulos, N., Stagg, J., Lejeune, L., Pommey, S., & Galipeau, J. Allogeneic marrow stromal cells are immune rejected by MHC class I and II mismatched recipient mice. *Blood* (2005).

32. Wang, Y., Chen, X., Armstrong, M. A., & Li, G. Survival of bone marrow-derived mesenchymal stem cells in a xenotransplantation model. *J Orthop. Res.*, (2007).

33. MacDonald, D. J. et al. Persistence of marrow stromal cells implanted into acutely infarcted myocardium: observations in a xenotransplant model. *J Thorac. Cardiovasc. Surg.* 130, 1114-1121 (2005).

34. Saito, T., Kuang, J. Q., Bittira, B., Al-Khaldi, A., & Chiu, R. C. Xenotransplant cardiac chimera: immune tolerance of adult stem cells. *Ann. Thorac. Surg.* 74, 19-24 (2002).

35. Zebardast, N. The Role of Human Umbilical Cord Perivascular Cells (HUCPVCs) in Dermal Wound Healing. 1-66. 2007. University of Toronto, Faculty of Applied Science and Engineering, Division of Engineering Science.
Ref Type: Thesis/Dissertation 36. Dawes, R. et al. Combinations of CD45 isoforms are crucial for immune function and disease. *J Immunol.* 2006, March 75. 3417-3425 (2006).

37. Hirschberg, H., Evensen, S. A., Henriksen, T., & Thorsby, E. The human mixed lymphocyte-endothelium culture interaction. *Transplantation* 19, 495-504 (1975).

We claim:

1. An in vivo method for treating a subject having or at risk of developing an adverse immune reaction, comprising administering to the subject a composition comprising an immunomodulating effective amount of the soluble fraction of medium conditioned by umbilical cord perivascular cells, wherein said adverse immune reaction is directed against biological material other than said composition and wherein said administering treats said subject by inhibiting or reducing said adverse immune reaction.

2. The method of claim 1, wherein the subject has or is at risk for graft versus host disease.

3. The method of claim 1, wherein the subject has or is at risk for a mixed lymphocyte reaction.

4. The method of claim 1, wherein the subject has or is at risk for graft rejection.

5. The method of claim 4, wherein the graft is a skin graft.

6. The method of claim 4, wherein the graft is an organ graft.

7. The method of claim 4, wherein the graft is a marrow graft.

8. The method of claim 4, wherein the graft is a peripheral blood graft.

9. The method of claim 1, wherein the subject has an autoimmune disorder.

10. The method of claim 1, wherein the subject is afflicted with a leukemia and is at risk for graft versus host disease.

11. The method of claim 1, wherein the umbilical cord perivascular cells are human umbilical cord perivascular cells (HUCPVCs).

12. The method of claim 1, wherein the umbilical cord perivascular cells comprise a transgene that encodes a protein of interest.

13. The method of claim 11, wherein the umbilical cord perivascular cells are substantially MHC double negative HUCPVCs.

14. The method of claim 1, wherein the second component comprises an unfractionated extract of medium conditioned by said cells that comprises said soluble fraction.

15. The method of claim 1, wherein the composition further comprises said umbilical cord perivascular cells.

16. The method of claim 15, wherein said umbilical cord perivascular cells are human umbilical cord perivascular cells (HUCPVCs).

* * * * *